(12) United States Patent
Radel et al.

(10) Patent No.: US 10,376,325 B2
(45) Date of Patent: Aug. 13, 2019

(54) CONTROL OF MULTIPLE DEVICES

(71) Applicant: Intuitive Surgical Operations, Inc., Sunnyvale, CA (US)

(72) Inventors: Joshua Radel, Sunnyvale, CA (US); Stanley Fung, Sunnyvale, CA (US); Jason Jiang, Sunnyvale, CA (US); Tabish Mustufa, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/742,303

(22) PCT Filed: Jul. 6, 2016

(86) PCT No.: PCT/US2016/041052
§ 371 (c)(1),
(2) Date: Jan. 5, 2018

(87) PCT Pub. No.: WO2017/007795
PCT Pub. Date: Jan. 12, 2017

(65) Prior Publication Data
US 2018/0206925 A1    Jul. 26, 2018

Related U.S. Application Data

(60) Provisional application No. 62/189,523, filed on Jul. 7, 2015.

(51) Int. Cl.
*G06F 8/60* (2018.01)
*G06F 8/65* (2018.01)
(Continued)

(52) U.S. Cl.
CPC ............. *A61B 34/35* (2016.02); *A61B 34/25* (2016.02); *A61B 34/37* (2016.02); *A61B 34/74* (2016.02);
(Continued)

(58) Field of Classification Search
CPC ...... B25J 1/00; B25J 9/18; B25J 11/00; A61B 1/00; A61B 17/00; A61B 18/18;
(Continued)

(56) References Cited

U.S. PATENT DOCUMENTS 6,132,368 A    10/2000 Cooper
6,246,200 B1    6/2001 Blumenkranz et al.
(Continued)

FOREIGN PATENT DOCUMENTS

WO    WO2013017673 A1    2/2013

OTHER PUBLICATIONS

J. Kramer and J. Magee, "Dynamic Configuration for Distributed Systems," in IEEE Transactions on Software Engineering, vol. SE-11, No. 4, pp. 424-436, Apr. 1985. (Year: 1985).*
(Continued)

*Primary Examiner* — Andrew M. Lyons
(74) *Attorney, Agent, or Firm* — Fish & Richardson P.C.

(57) ABSTRACT

Methods, systems, and apparatuses for controlling surgical systems. In one aspect, a method includes obtaining, at a control subsystem associated with a surgical system, hardware configuration information from a first patient side subsystem that is communicatively coupled to and controlled by the control subsystem; determining a software version to be used by the control subsystem and the first patient side subsystem, wherein determining the software version includes selecting the software version from among a plurality of software versions, and wherein each software version of the plurality of software versions is associated with a particular patient side subsystem; instructing the first patient side subsystem to use the software version; determining whether the software version is currently loaded on the control subsystem; in response to determining that the software version is not currently loaded on the control
(Continued)

subsystem, loading the software version on the control subsystem; and initializing the surgical system.

16 Claims, 8 Drawing Sheets

(51) Int. Cl.
*A61B 17/00* (2006.01)
*A61B 34/00* (2016.01)
*A61B 34/10* (2016.01)
*A61B 34/30* (2016.01)
*A61B 34/35* (2016.01)
*A61B 34/37* (2016.01)
*A61B 90/90* (2016.01)
*G06F 19/00* (2018.01)

(52) U.S. Cl.
CPC .............. *G06F 8/60* (2013.01); *G06F 8/65* (2013.01); *G06F 19/00* (2013.01); *A61B 34/10* (2016.02); *A61B 90/90* (2016.02); *A61B 2017/00199* (2013.01); *A61B 2017/00212* (2013.01); *A61B 2017/00221* (2013.01); *A61B 2017/00225* (2013.01); *A61B 2034/258* (2016.02); *A61B 2034/304* (2016.02); *A61B 2034/743* (2016.02); *A61B 2034/744* (2016.02)

(58) Field of Classification Search
CPC ..... A61B 19/00; A61B 19/19; A61B 19/2203; G05B 15/00; G06F 19/00
USPC ......... 128/849–856, 897–899, 923; 269/238, 269/297; 318/566, 568.11, 568.12, 318/568.16, 568.17, 568.18, 568.19, 318/568.2, 568.21, 568.22, 568.25, 574, 318/628; 348/45, 51; 359/399; 379/88.14; 414/1, 2, 4, 5, 7; 600/101–104, 106, 117, 118, 131, 424, 600/427, 429, 595; 601/1; 606/1, 45, 46, 606/102, 111, 130, 587; 607/3, 9, 17; 700/245–251, 256–264; 701/245, 701/257–259, 264, 450; 901/1–3, 8–11, 901/14–17, 20, 27–30, 33, 34, 41, 46
See application file for complete search history.

(56) References Cited

U.S. PATENT DOCUMENTS

| | | | |
|---|---|---|---|
| 6,714,839 B2 | 3/2004 | Salisbury, Jr. et al. | |
| 6,728,599 B2 | 4/2004 | Wang et al. | |
| 6,793,653 B2 | 9/2004 | Sanchez et al. | |
| 7,048,745 B2 | 5/2006 | Tierney et al. | |
| 7,363,484 B2* | 4/2008 | Davis | G06F 9/4405 713/1 |
| 7,567,886 B2* | 7/2009 | Beeston | G06F 15/177 702/182 |
| 8,521,331 B2 | 8/2013 | Itkowitz | |
| 8,527,094 B2 | 9/2013 | Kumar et al. | |
| 9,186,518 B2* | 11/2015 | Kothandaraman | A61N 1/37235 |
| 9,229,731 B2* | 1/2016 | Domsch | G06F 9/4416 |
| 9,582,656 B2* | 2/2017 | Russo | G06F 21/44 |
| 2001/0027517 A1* | 10/2001 | Kato | G06F 8/65 713/1 |
| 2003/0159135 A1* | 8/2003 | Hiller | G06F 9/44536 717/166 |
| 2004/0186345 A1 | 9/2004 | Yang et al. | |
| 2005/0251156 A1 | 11/2005 | Toth et al. | |
| 2006/0047365 A1* | 3/2006 | Ghodoussi | G06F 19/3418 700/251 |
| 2007/0013336 A1 | 1/2007 | Nowlin et al. | |
| 2007/0168571 A1* | 7/2007 | Ramsey | G06F 8/65 710/8 |
| 2007/0173975 A1 | 7/2007 | Schena | |
| 2008/0154957 A1* | 6/2008 | Taylor | G06F 9/4411 |
| 2008/0301665 A1* | 12/2008 | Charlton | A61B 5/14532 717/170 |
| 2009/0150865 A1* | 6/2009 | Young | G16H 40/40 717/120 |
| 2009/0163928 A1 | 6/2009 | Schena | |
| 2010/0094981 A1* | 4/2010 | Cordray | H04L 69/40 709/222 |
| 2010/0235373 A1* | 9/2010 | Holden | G06F 13/385 707/758 |
| 2011/0126044 A1* | 5/2011 | Kim | G06F 8/63 714/6.12 |
| 2011/0179405 A1* | 7/2011 | Dicks | G06F 8/61 717/168 |
| 2011/0282356 A1 | 11/2011 | Solomon et al. | |
| 2013/0104120 A1* | 4/2013 | Arrizza | G06F 8/65 717/173 |
| 2013/0191032 A1* | 7/2013 | Marquardt | G06F 11/0796 702/19 |
| 2013/0325030 A1 | 12/2013 | Hourtash et al. | |
| 2014/0236894 A1 | 8/2014 | Hoffman et al. | |
| 2014/0257330 A1 | 9/2014 | Choi et al. | |
| 2014/0281466 A1* | 9/2014 | Samuel | G06F 9/4408 713/2 |
| 2015/0038983 A1 | 2/2015 | Wang et al. | |
| 2015/0073498 A1* | 3/2015 | Kothandaraman | A61N 1/3605 607/59 |
| 2015/0199192 A1* | 7/2015 | Borges | G06F 8/65 717/172 |
| 2016/0213537 A1* | 7/2016 | Hayes | G06Q 50/22 |
| 2016/0253471 A1* | 9/2016 | Volpe | A61N 1/3968 607/5 |

OTHER PUBLICATIONS

H. Mitsumaki, T. Ikeda, R. Kodama and T. Aizono, "Modularized system architecture for flexible clinical laboratory systems," Proceedings 5th International Symposium on Autonomous Decentralized Systems, Dallas, TX, USA, 2001, pp. 111-118. (Year: 2001).*
Edited Transcript of ISRG presentation Jun. 10-15 6:20pm GMT, Intuitive Surgical Inc at Goldman Sachs Healthcare Conference, Jun. 11, 2015. [online] Jun. 23, 2015, Retrieved from the Internet:< URL: http://finance.yahoo.com/news/edited-transcript-isrg-presentation-10-113206307.html> (last visited Jun. 23, 2015).
International Search Report and Written Opinion for Application No. PCT/US16/41052, dated Oct. 21, 2016, 21 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
European Application No. 16821895.6, Extended European Search Report dated Feb. 11, 2019, 12 pages.

* cited by examiner

US 10,376,325 B2

CONTROL OF MULTIPLE DEVICES

CROSS REFERENCE TO RELATED APPLICATIONS

This application is a U.S. National Phase Application under 35 U.S.C. § 371 of International Patent Application No. PCT/US2016/041052, filed Jul. 6, 2016, which claims priority to U.S. Provisional Patent Application No. 62/189,523, filed on Jul. 7, 2015, the entire contents of which are hereby incorporated by reference.

BACKGROUND

This specification relates to control systems.

Minimally invasive medical techniques are aimed at reducing the amount of extraneous tissue that is damaged during diagnostic or surgical procedures, thereby reducing patient recovery time, discomfort, and harmful side effects. Millions of surgeries are performed each year in the United States. Many of these surgeries can potentially be performed in a minimally invasive manner.

Minimally invasive systems for use in surgery can be teleoperated, robotic, or both teleoperated and robotic. Teleoperated refers to acting at a distance to control a machine. In a teleoperated surgical system, the surgeon uses a controller to control a surgical instrument inserted into a body cavity rather than directly holding and moving the instrument by hand.

SUMMARY

In general, one innovative aspect of the subject matter described in this specification can be embodied in methods that include the actions of obtaining, at a control subsystem associated with a surgical system, hardware configuration information from a first patient side subsystem of the surgical system that is communicatively coupled to and controlled by the control subsystem; determining a software version to be used by the control subsystem and the first patient side subsystem, wherein determining the software version includes selecting the software version from among multiple software versions, and wherein each software version of the multiple software versions is associated with a particular patient side subsystem; instructing the first patient side subsystem to use the software version; determining whether the software version is currently loaded on the control subsystem; in response to determining that the software version is not currently loaded on the control subsystem, loading the software version on the control subsystem; validating the software version loaded on the control subsystem and the first patient side subsystem; and initializing the surgical system with the software version.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. The method includes validating the hardware configuration of the first patient side subsystem prior to determining the software version. Validating the hardware configuration included determining that the hardware configuration is compatible with the control subsystem. The control subsystem comprises components of a surgeon console of the surgical system, wherein the surgeon console is configured to provide control functions to an operator of the surgical system. The first patient side subsystem includes one or more manipulators configured to hold and position one or more corresponding surgical instruments.

Loading the software version on the first patient side subsystem includes: determining a particular boot image of multiple boot images, wherein the particular boot image contains the software version; and rebooting the first patient side subsystem from a current boot image to the particular boot image. Rebooting the first patient side subsystem from the current boot image to the particular boot image comprises: obtaining a first header block for the particular boot image; restoring the obtained first header block to the particular boot image; storing a copy of a second header block for the current boot image; and after restoring and storing, invalidating the second header block for the current boot image. Rebooting the first patient side subsystem from the current boot image to the particular boot image comprises: storing a parameter identifying the particular boot image; reading, by a boot loader, the stored parameter; and selecting, by the boot loader, the particular boot image based on the stored parameter. Loading the software version on the first patient side subsystem comprises: determining one or more particular modules of multiple modules, wherein the particular modules contain the software version; and loading the particular modules.

The determining the software version is based on a collaboration between the control subsystem and the first patient-side subsystem. Validating the software version includes: determining whether the control subsystem and the first patient side subsystem have loaded the software version; and in response to determining that one or more of the control subsystem or the first patient side subsystem has not loaded the determined software version, generating an error message and preventing initialization of at least the subsystem for use in the surgical system.

The method includes coupling one or more accessory devices to the surgical system, wherein the one or more accessory devices are not specific to the first patient side subsystem. The method further includes: recognizing that a second patient side subsystem has been communicatively coupled to the controller subsystem; obtaining hardware information about the second patient side subsystem; validating the hardware information of the second patient side subsystem; and instructing the second patient side subsystem to load the determined software version. The method further includes: recognizing that a second patient side subsystem has been communicatively coupled to the control subsystem; obtaining hardware information about the second patient side subsystem; validating the hardware information of the second patient side subsystem; and loading a second software version on the control subsystem, wherein the second software version corresponds to software loaded on the second patient side subsystem. The software version is determined based on software version currently loaded on the controller subsystem. The software version is determined based on a software version currently loaded on the first patient-side subsystem.

In general, one innovative aspect of the subject matter described in this specification can be embodied in methods that include the actions of receiving, at a first subsystem of a surgical system, an instruction to load a particular software version on the first subsystem, wherein the particular software version is one of multiple software versions associated with respective subsystems of multiple subsystems, and wherein the first subsystem comprises multiple configurations including a first configuration that is currently configured on the first subsystem; determining that the particular software version is located on a second configuration; storing data corresponding to the second configuration; configuring the subsystem to the second configuration; and loading the particular software version.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. The method includes downloading the second configuration in response to receiving the instruction to load the particular software version. The first configuration comprises a first boot image, the second configuration comprises a second boot image, and wherein storing data corresponding to the second configuration comprises: restoring a first header block for the second boot to make the second boot image valid; storing a copy of a second header block for the first boot image; and after the restoring and the storing, invalidating the header block of the first boot image.

In response to an interrupt prior to configuring the subsystem: determining a valid boot image from the first boot image and the second boot image; rebooting the subsystem to the valid boot image; determining whether the valid boot image is the second boot image; and in response to a determination that the valid boot image is not the second boot image, restoring of the first header block to the second boot image, invalidating the header block of the first boot image, and rebooting the subsystem to the second boot image.

The first configuration comprises a first boot image, the second configuration comprises a second boot image, and wherein rebooting the subsystem to the second configuration comprises: rebooting the subsystem to the second configuration reading, by a boot loader, the stored data; and selecting by the boot loader, the second boot image based on the stored data. The first configuration comprises a first set of modules, the second configuration comprises a second set of modules, and wherein configuring the subsystem to the second configuration comprises loading the particular modules.

In general, one innovative aspect of the subject matter described in this specification can be embodied in systems that include multiple subsystems including: a control subsystem, a first patient-side subsystem, and a second patient-side subsystem, wherein the first patient-side subsystem is associated with a first software configuration and the second patient-side subsystem is associated with a second software configuration distinct from the first software configuration, wherein the control subsystem configures the system, wherein configuring the system includes determining whether a first combination of the control subsystem and the first patient side subsystem or a second combination of the control subsystem and the second patient side subsystem is communicatively coupled together and, in response to the determining, selecting a particular software configuration to be used by the first or second combination and initializing the system after validating the software configuration.

The foregoing and other embodiments can each optionally include one or more of the following features, alone or in combination. Configuring the system includes loading the determined software configuration on the control subsystem. The first patient-side subsystem has a first hardware configuration and wherein the control subsystem determines the first hardware configuration is valid for a system comprising the control subsystem and the first patient-side subsystem prior to determining the particular software configuration. In the first combination the first patient-side subsystem is communicatively coupled to the control subsystem and wherein configuring the system includes transmitting instructions from the control subsystem to the first patient-side subsystem to load the determined software configuration. The control subsystem comprises components of a surgeon console of the surgical system, wherein the surgeon console is configured to provide control functions to an operator of the surgical system.

In general, one innovative aspect of the subject matter described in this specification can be embodied in methods that include the actions of selecting a first patient side subsystem to communicatively couple to a control subsystem, wherein the first patent side subsystem is selected from a plurality of patient side subsystems, wherein each patient side subsystem has a distinct default software configuration; configuring a surgical system comprising the control subsystem and the first patient side subsystem, wherein configuring the surgical system includes: determining a particular software configuration to be used by each of the control subsystem and the first patent side subsystem; in response to determining that the particular software configuration is different form a first software configuration currently loaded on the first patent side subsystem, instructing the first patient side subsystem to use the particular software version; and in response to determining that the particular software configuration is different form a second software configuration currently loaded on the control subsystem, loading the particular software configuration on the control subsystem; and initializing the surgical system with the particular software version. Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

In general, one innovative aspect of the subject matter described in this specification can be embodied in methods that include the actions of providing surgical functionality with a first control subsystem and a first patient side subsystem of a surgical system; selecting for communicative coupling to the surgical system while the surgical system is providing the surgical functionality, a new surgical subsystem that is one of a group consisting of a second control subsystem and a second patient side subsystem; and adding, while the surgical system is providing the surgical functionality, the new surgical subsystem to the surgical system without interrupting the surgical functionality by: determining that a particular software configuration used by the surgical system is not loaded on the new surgical subsystem; and loading the particular software configuration on the new surgical subsystem while maintaining surgical functionality with the first control subsystem and a first patient side subsystem.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. Loading the particular software configuration on the new surgical subsystem comprises: determining a particular boot image of multiple boot images, wherein the particular boot image contains the particular software configuration; and rebooting the new surgical subsystem from a current boot image to the particular boot image. Rebooting the new surgical subsystem from a current boot image to the particular boot image comprises: obtaining a first header block for the particular boot image; restoring the obtained first header block to the particular boot image; storing a copy of a second header block for the current boot image; and after restoring and storing, invalidating the second header block for the current boot image. Rebooting the new surgical subsystem from a current boot image to the particular boot image comprises: storing a parameter identifying the particular boot image; reading, by a boot loader, the stored parameter; and selecting, by the boot loader, the particular boot image based on the stored parameter. Loading the particular software configuration on the new surgical subsystem comprises: determining one or more particular modules of multiple modules, wherein the particular modules contain the particular configuration; and loading the particular modules. Determining that a particular software configuration used by the surgical system is not loaded on the new surgical subsystem is based on the particular software configuration currently loaded on the first control subsystem. Determining that a particular software configuration used by the surgical system is not loaded on the new surgical subsystem is based on the particular software configuration currently loaded on the first patient side subsystem.

Particular embodiments of the subject matter described in this specification can be implemented so as to realize none, one or more of the following advantages. A surgical system having multiple subsystems can be setup and configured to use a common software version. Consequently, subsystems having different hardware and software configurations can be used in a common system such that a provider does not need to obtain multiple full separate surgical systems. Hardware and software configurations are validated to prevent a surgical system from operating in an invalid configuration.

The ability to use different hardware and subsystems and software configurations provides testing advantages for a manufacturer. When there are multiple hardware subsystems in field, with multiple software configurations of each, the testing burden for the manufacturer can be very high. In conventional systems, in order to allow customers to use the hardware and software interchangeably, the manufacturer has to test all of the possible combinations. The ability to re-program and/or re-configure a system after coupling together multiple subsystems as described in this specification allows one particular subsystem be used in different system configurations without having to test all possible combinations. Each valid combination of subsystems has a particular tested software version associated with it, and the subsystems reconfigure on the fly to that software version.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Minimally invasive surgery is performed by inserting a surgical instrument through a port in a patient's body. In some implementations, the surgical instrument is at least partially teleoperated by a surgeon using a surgeon console. In a teleoperated surgical system, the surgeon is provided with an image of the surgical site, e.g., using stereoscopic images. While viewing the surgical site on a suitable viewer or display, the surgeon performs the surgical procedures on the patient by moving one or more control input devices, which in turn control the motion of corresponding teleoperated surgical instruments.

The teleoperated surgical instruments are typically inserted through one or more ports to, for example, treat tissues at surgical sites within the patient. A port is a general term indicating the location at which a surgical instrument enters the patient body. The port can be artificially created or a natural opening. For example, the port can result from an incision or can correspond to a natural body orifice, e.g., the mouth.

A surgical system typically includes two or more subsystem components. The subsystem components may include one or more patient-side subsystems that hold and position surgical instruments, one or more control console subsystems used by a surgeon to control surgical instruments held by a patient-side subsystem, and one or more auxiliary equipment units that can include equipment associated with the surgical system, such as camera control equipment for one or more cameras used to capture surgical field images, surgical field illumination equipment, electrosurgical energy generation, central or distributed data processing equipment for the surgical system, and the like. In some implementations, a control console is also used to manage the setup and configuration of the surgical system. An example surgical system is the da Vinci® Xi™ Surgical System (model IS4000), commercialized by Intuitive Surgical, Inc., Sunnyvale, Calif.

Figure 1:
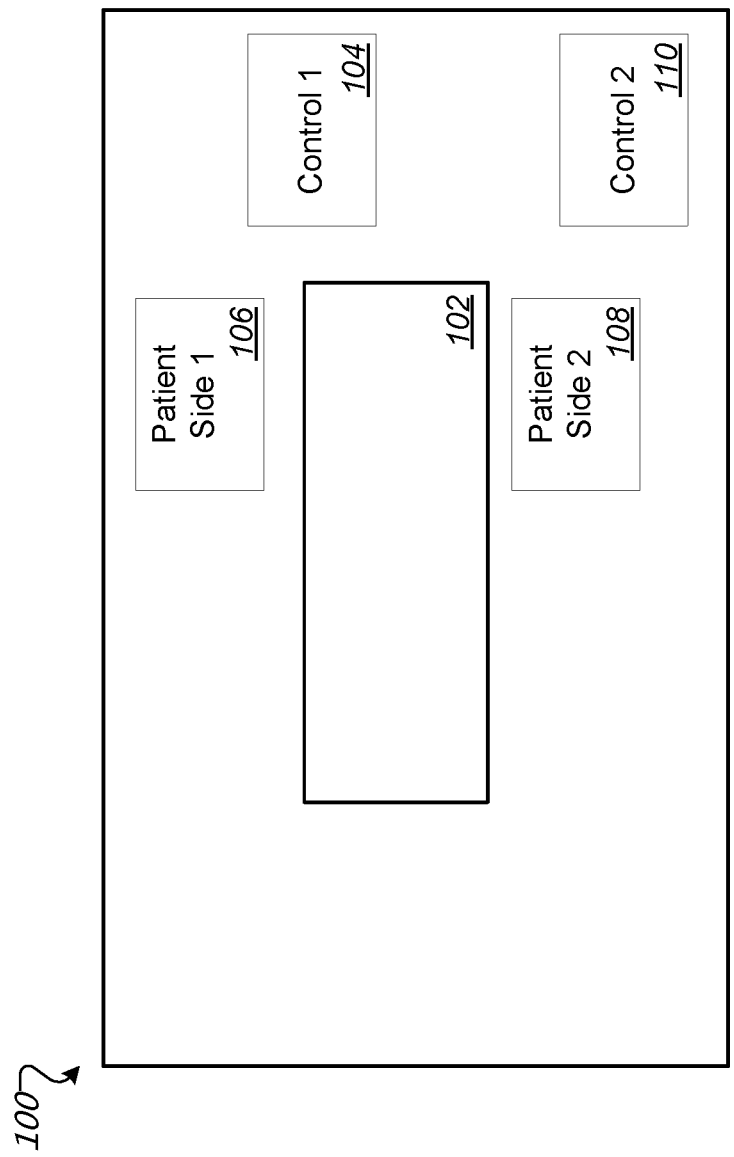
FIG. 1 shows a plan view of an example environment for performing teleoperated surgery.

FIG. 1 shows a plan view of an example environment 100 for performing teleoperated surgery. The environment 100 can be, for example, an operating room environment. The environment 100 includes an operating table 102, a first control console 104, a first patient-side subsystem 106, a second patient-side subsystem 108, and in this example, an optional second control console 110.

The first and second patient-side subsystems 106 and 108 each support one or more surgical instruments or cameras. For example, the first patient-side subsystem 106 is a patient-side subsystem that includes one or more manipulators each holding a corresponding surgical instrument. The movement of a tip of each surgical instrument is controlled by the first control console 104, e.g., in response to a user input to one or more corresponding controllers. The manipulators can be robotic, teleoperated, or both.

The second patient-side subsystem 108 can be similar to the first patient-side subsystem. For example, the second patient-side subsystem 108 can include a camera for providing visualization of the surgical field within the patient. The second patient-side subsystem 108 can include an endoscope that can be inserted into a body cavity to provide visualization of a surgical field. The view of the surgical field can be provided to the control console 104. In some implementations, the second patient-side subsystem 108 can include both a camera and one or more manipulators for holding and positioning corresponding surgical instruments.

The first control console 104 is a surgeon console used to control one or more surgical devices as part of a surgical procedure performed on a patient located on the table 102. The first control console 104 is used to control the movement of one or more surgical instruments to perform a particular surgical procedure. The first control console 104 can include one or more controllers used by a surgeon to control corresponding surgical instruments. For example, first control console 104 can include hand controls that can be moved to manipulate a corresponding surgical instrument. In some implementations, the first control console 104 also includes a viewer that provides an image of a surgical field provided by one or more cameras. The second control console 110 is typically configured in a manner similar to the first control console 104, and it can be used to provide control patient-side subsystem manipulators by a second operator, for example, for training a surgeon at the first control console 104 or for performing complex procedures by providing control inputs in addition to the control inputs from the first control console 104.

Various teleoperated patient-side subsystems exist, each having a unique hardware configuration and associated control requirements. For example, one teleoperated patient-side surgical system may be a multi-port surgical system, in which each surgical instrument enters the patient's body through a unique corresponding port. An example multi-port system is disclosed in U.S. Patent Application Pub. No. US 2013/032503 A1 (filed May 31, 2013). A second teleoperated patient-side surgical system may be a single-port surgical system, in which all surgical instruments enter the patient's body through a single port. An example single-port system is disclosed in U.S. Patent Application Pub. No. US 2011/0282356 A1 (filed Aug. 12, 2010). Patient-side surgical systems may include single- or multiple-arm systems, with arms mounted in various locations, such as those disclosed in U.S. Patent Application Pubs. No. US 2004/0186345 A1 (filed Dec. 15, 2003), US 2007/0013336 A1 (filed May 19, 2005), US 2007/0173975 A1 (filed Jan. 15, 2007), and US 2009/0163928 A1 (filed Dec. 21, 2007).

Likewise, various teleoperated control subsystems may exist, each having a unique configuration, and each typically designed to control a single patient-side subsystem so that the unique control subsystem and patient-side subsystem pair (along with any additional auxiliary equipment) forms a single teleoperated surgical system. For example, U.S. Pat. No. 6,132,368 (filed Nov. 21, 1997), U.S. Pat. No. 6,246,200 (filed Aug. 3, 1999), U.S. Pat. No. 6,714,839 B2 (filed Sep. 17, 1999), U.S. Pat. No. 6,793,653 B2 (filed Dec. 8, 2001), and U.S. Pat. No. 8,521,331 B2 (filed Nov. 13, 2009) disclose teleoperated control subsystems.

A single teleoperated surgical system may include more than one teleoperated control subsystem. For example, U.S. Pat. No. 6,728,599 B2 (filed Sep. 7, 2001), and U.S. Pat. No. 8,527,094 B2 (filed Dec. 27, 2005) disclose two or more control subsystems, each separately operated by a corresponding surgeon, and the two control subsystems together being associated with controlling a single teleoperated surgical system. The use of two or more control subsystems facilitates one surgeon training another, or it facilitates two surgeons working together if the number of teleoperated surgical devices in the patient-side subsystem is more than one surgeon can control alone.

Thus in known surgical systems, a single patient-side subsystem (which may include one or more separate components), is controlled by one or more control subsystems that are uniquely associated with the single patient-side subsystem. But, if a health care provider desires two or more patient-side subsystems, each with a unique hardware architecture and associated control software configurations, various reasons such as economy may prevent the provider from acquiring the two surgical systems.

Therefore, in one aspect it is desirable to have a single control subsystem hardware configuration that can be used with two or more uniquely configured patient-side subsystems. For example, the single control subsystem and a first patient-side subsystem together form a first teleoperated surgical system, and the single control system and a second patient-side subsystem together form a second teleoperated surgical system.

Similarly, in another aspect it is desirable to have two or more control subsystems, each with similar or identical hardware configurations, that together can be used with two or more uniquely configured patient-side subsystems. For example, the two or more control systems and a first patient-side subsystem together form a first teleoperated surgical system, and the two or more control systems and a second patient-side subsystem together form a second teleoperated surgical system.

In yet another aspect, it is desirable to have a single control subsystem hardware configuration, or two or more control system hardware configurations working together, that can be used with surgical system subsystems other than patient-side subsystems that control surgical instruments. For example, the single control subsystem and a first auxiliary subsystem together form a first teleoperated surgical system, and the single control system and a second auxiliary subsystem together form a second teleoperated surgical system. Likewise, two or more control subsystems and a first auxiliary subsystem together form a first teleoperated surgical system, and the two or more control subsystems and a second auxiliary subsystem together form a second teleoperated surgical system.

And in still another aspect, it is desirable to have techniques for determining and implementing a uniform software configuration between surgical system subsystems that form two or more unique surgical systems, regardless of a current software and/or hardware configuration of the system or subsystems.

Figure 2:
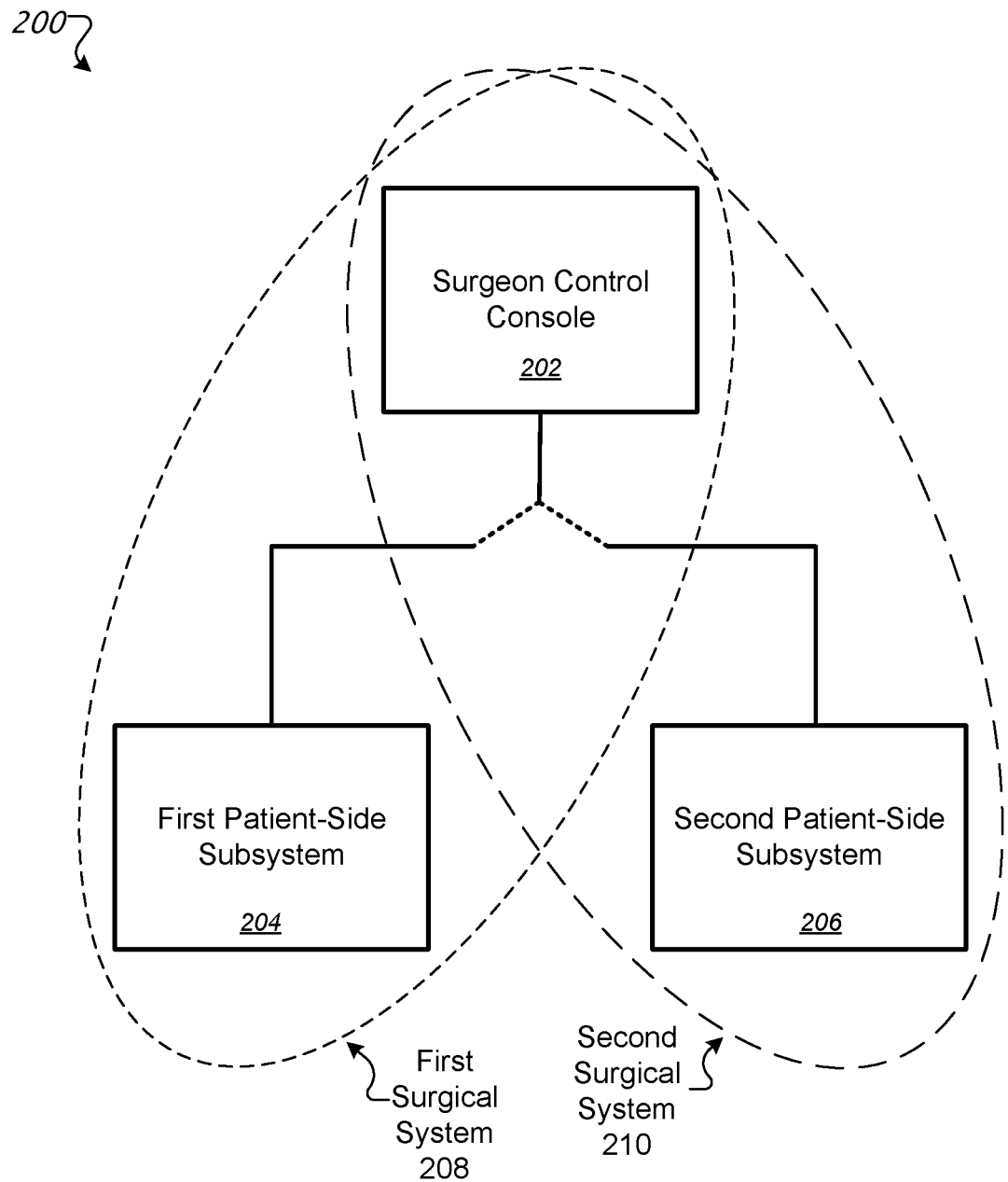
FIG. 2 is a diagram of example systems coupling subsystems associated with different surgical systems

FIG. 2 is a diagram 200 of example systems coupling subsystems associated with different surgical systems. In particular, FIG. 2 illustrates a control console 202, a first patient-side subsystem 204, and a second patient-side subsystem 206. For purposes of illustration, the first patient-side subsystem 204 and the second patient-side subsystem 208 are each associated with different hardware and software configurations, e.g., particular software versions, associated with different surgical system models. Using techniques for reprogramming on the fly as described in detail below with respect to FIGS. 3-6, multiple systems can be configured and operated using the surgeon control console 202 and either the first patient-side subsystem 204 or the second patient-side subsystem 206.

For example, a first surgical system 208 can be formed by coupling the surgeon control console 202 with the first patient-side subsystem 204 and configuring the system to operate according to a particular software configuration. A second surgical system 210 can be formed by coupling the surgeon control console 202 with the second patient-side subsystem 206 and configuring the system to operate according to a particular software configuration. The particular software configuration of the second surgical system 210 may be distinct from the particular software configuration of the first surgical system 208. For example, the particular software configuration of the first surgical system 208 may be a first software version associated with the particular hardware of the first patent-side subsystem 204 while the particular software configuration of the second surgical system 210 may be a second software version associated with the surgeon control console 202 and loaded on the second patient-side subsystem 206.

Each patient-side subsystem can be coupled to the surgeon control console to form the particular surgical system using one or more data links that may be wired or wireless. Each of these surgical systems are possible given a valid hardware configuration for each patient-side subsystem and determination of a common software version to use for all subsystems of the system as described below. In some implementations, the first patient-side subsystem 204 and the second patient-side subsystem 206 have a same hardware configuration but different software versions. In some other implementations, the first patient-side subsystem 204 and the second patient-side subsystem 206 have different hardware configurations and different software versions. Additionally, by determining a valid configuration as each system is formed, all possible software configurations do not need to be tested. Although not shown in FIG. 2, further systems can be formed based on additional patient-side subsystems or additional surgeon control consoles or additional auxiliary equipment units.

In some cases, another surgeon control console or another patient-side sub-system can connect after setup of the surgeon control console 202 and/or patient-side subsystems 204. For example, the surgeon control console 202 and/or patient-side subsystems 204 may be used in an operation, when it is discovered that another surgeon control console or another patient-side sub-system is needed. For example, another surgeon control console may be needed to allow a second surgeon to observe or assist in a surgical task. In another example, another patient-side subsystem may be needed to provide a surgical tool not provided by either of the existing patient-side subsystems 204 or 206.

In such a situation, updating the software of the newly added system may be required. As will be described with greater detail below, the rest of the system may remain usable while the newly added system is updated.

Figure 3:
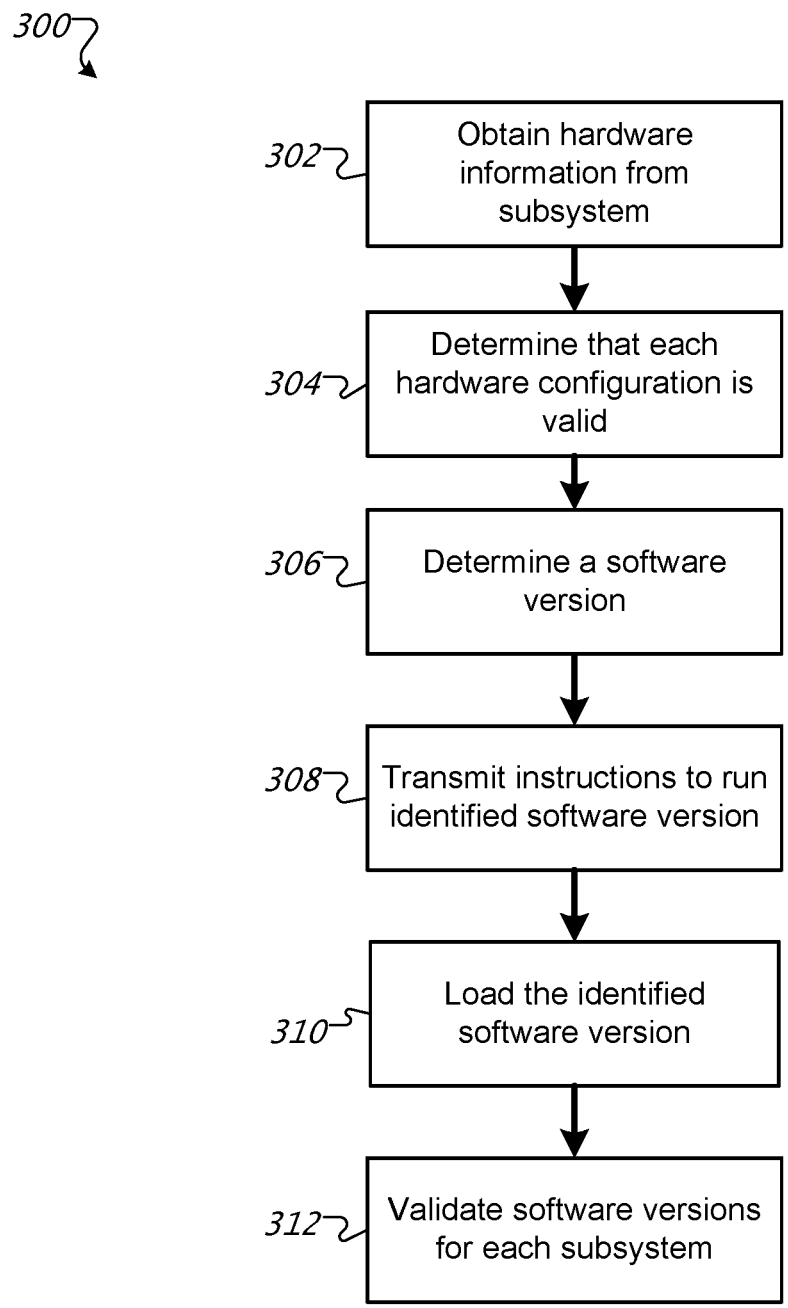
FIG. 3 is a flow diagram of an example process for configuring control consoles and other subsystems to be used together in a surgical system.

FIG. 3 is a flow diagram of an example process 300 for configuring control consoles and other subsystems to be used together in a surgical system. The process 300 can be performed, in this example, by a control console such as first control console 104 of FIG. 1. However, a similar process could be used by a particular subsystem that is designated as controlling setup and configuration of the surgical system.

Hardware configuration information is obtained from each of one or more subsystems (step 302). For example, the control console can have a hardware configuration associated with a first surgical system model. A second different subsystem, e.g., a patient side subsystem, can have a hardware configuration associated with a second surgical system model. Alternatively, subsystems can have the same hardware configuration but different software configurations.

In some implementations, when the subsystems are coupled to the control console and the control console is activated, the control console sends a request to each subsystem for the hardware configuration of that subsystem. In some other implementations, when the subsystems are coupled to the control console, each respective subsystem broadcasts the hardware configuration for that subsystem to a corresponding control console.

A determination is made that the hardware configuration of each of the one or more subsystems is valid (step 304). In some implementations, the determination includes comparing an identifier of the hardware received from each subsystem to a lookup table of hardware configurations that are compatible with the control console. For example, particular hardware designs may be incompatible with particular control hardware of the control console. In another example, hardware from another manufacturer may not be authorized to be paired with the control console.

If a determination is made that the hardware configuration of a particular subsystem is not valid, then an error is generated. The error can prevent the subsystem from being controlled by the control console. Errors can be reported on the control console. Errors may also be reported to individual subsystems.

In response to determining that the hardware configuration for each subsystem is valid, a software version to execute on all subsystems including the control console is determined (step 306). The common software version to be executed by the subsystems can be determined in a variety of ways. In some implementations, each hardware configuration is associated with a default software configuration. If all subsystems are associated with the same default software configuration than that software configuration can be maintained. Determining the software version can include selecting the software version from among multiple software versions, and wherein each software version is associated with a particular subsystem.

In some implementations, the default software configuration of a particular subsystem determines the software configuration to be used for the entire surgical system. For example, the default software configuration of a subsystem acting as a patient cart and including one or more manipulators for holding respective surgical instruments can determine the software configuration to be used by the control console as well as other subsystems, e.g., a vision cart. In some implementations, the software configuration of the control console can control the software configuration to be used by all subsystems. Finally, when multiple subsystems are included in the system, a software configuration associated with the largest number of individual subsystems can be designated as the software configuration to be used by all subsystems.

In some implementations, each subsystem provides additional information to the control console indicating, for example, the software versions supported by the corresponding hardware configuration. The control console can use this additional information to determine which software version to use for the system.

In some alternative implementations, a cooperative technique is used in which no particular subsystem is designated the leader, but they negotiate with one another to see if a particular combination of hardware and software between the subsystems is designated as a valid and tested configuration.

Once the software version is determined, instructions are transmitted by the control console to each subsystem identifying the software version to execute (step 308). In some implementations, each subsystem receiving instructions determines whether the software version is the current software version. If the current version is not the determined software version, the subsystem loads the determined software version. The software versions can be stored on separate disk images.

If the determined software version is not currently loaded on the control console, the control console can be configured to reboot to load the determined software version (step 310). In some implementations, the control console includes multiple disk images. Each disk image includes a particular software version. Loading a particular software version is described below with respect to FIGS. 5-6.

The software version loaded on each subsystem is validated (step 312). In particular, validation determines that the correct software version has been loaded to each subsystem. If the correct software version has not been loaded, an error can be generated that prevents operation of the surgical system until resolved. In some implementations, the control console validates each subsystem. In some implementations, each subsystem performs a self-validation and reports results to the control console. Following validation, the surgical system can be initialized with the loaded software version. The initialized surgical system can be used, for example, to perform one or more surgical procedures.

Figure 4:
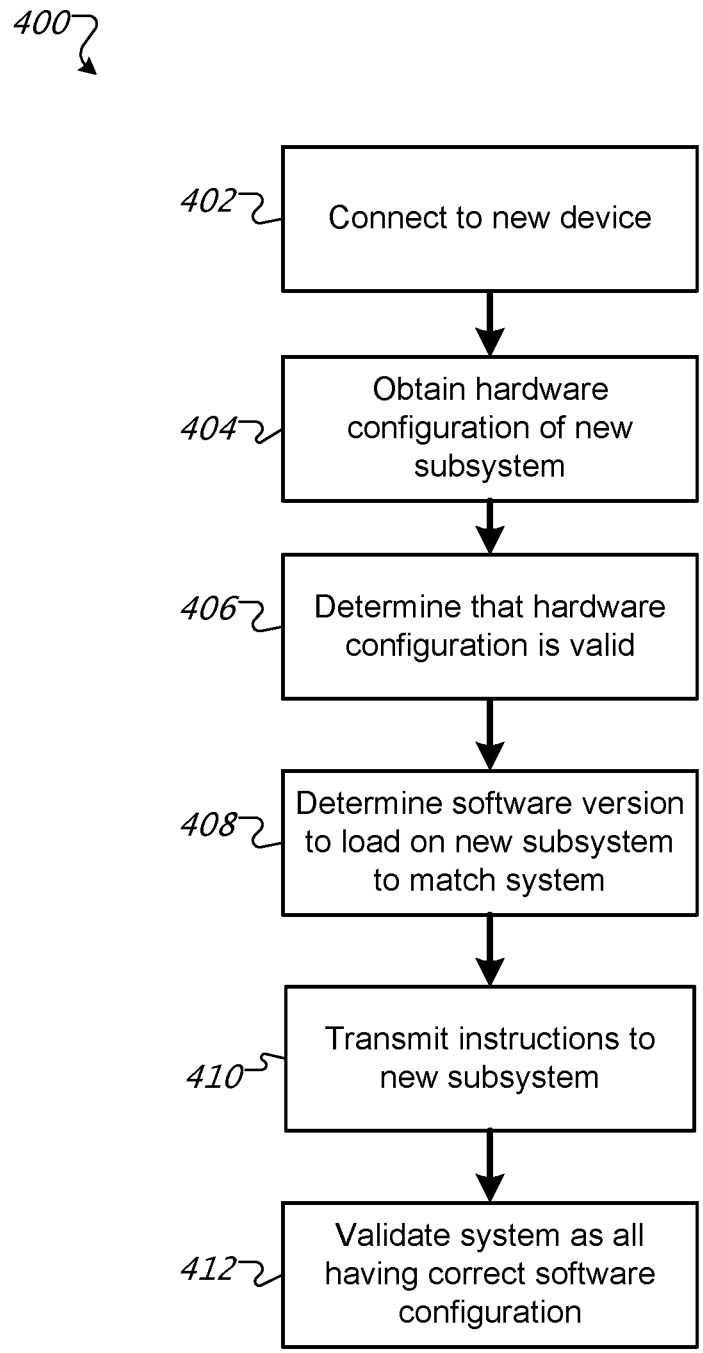
FIG. 4 is a flow diagram of an example process for adding a new subsystem to a preconfigured surgical system.

FIG. 4 is a flow diagram of an example process 400 for adding a new subsystem to a configured surgical system. The process 400 can be performed, in this example, by a control console such as first control console 104 of FIG. 1. However, a similar process could be used by any suitable subsystem.

A new subsystem is communicatively coupled to the surgical system (e.g., communicatively coupled to a control console of the surgical system) (step 402). For example, a surgical system can be initially set up in an environment, e.g., environment 100, as including a control console and a first subsystem that includes one or more manipulators for holding and positioning one or more surgical instruments. The surgical system can be setup for a particular software version as described above with respect to FIG. 3. At some later point an additional subsystem can be added. For example, an additional subsystem having corresponding manipulators may be required for a portion of a surgical procedure.

The hardware configuration for the new subsystem is obtained (404). In some implementations, when the new subsystem is coupled to the control console, the control console sends a request to the subsystem for the hardware configuration of that subsystem. In some implementations, when the new subsystem is coupled to the control console, the subsystem automatically reports the hardware configuration for that subsystem to the control console.

A determination is made that the hardware configuration of the new subsystem is valid (step 406). As described above with respect to FIG. 3, in some implementations, the determination includes comparing an identifier associated with the hardware of the new subsystem as against a lookup table of hardware configurations that are compatible with the control console.

In response to determining a valid hardware configuration for the new subsystem, the software version to load on the new subsystem to match the software version of the surgical system is determined (step 408). Since the surgical system was previously configured, the determination can include determining the current software version of the control console and/or one or more subsystems current configured and coupled to the control console.

Once the software version is determined, instructions are transmitted by the control console to the new subsystem identifying the software version to execute (step 410). In some implementations, the new subsystem determines whether the software version is the current software version of the new subsystem. If the current version is not the determined software version, the new subsystem loads the determined software version.

The control console validates the software configuration for the new subsystem (step 412). In particular, the validation determines that the correct software version has been loaded to the new subsystem. In some implementations, the validation is performed for all subsystems prior to using the surgical system.

While the new subsystem is being configured, it may be put into an error state in which the control console is not able to communicate with or control the subsystem. However, the control console and the old subsystem may be operable and continue to provide surgical functionality while the new subsystem is in the error state. That is, the control console and first subsystem may be used by the surgeon while waiting for the new subsystem to complete its configuration process.

While this updating may be done in pre-surgery setup, this functionality may be of particular importance if a new subsystem is to be added in the middle of surgery. For example, a complication may occur in the middle of a surgery, resulting in a determination that a new subsystem is needed. A second view angle may be needed, and thus a second view cart may be needed. In another example, an additional surgical implement may be needed to perform an unexpected procedure, and a patient side car with the needed implement may be added. In these cases, the use of these techniques may allow the addition of the new cart without interrupting the surgical functionality of the existing control console and existing subsystems.

In some implementations, rather than instructing the new subsystem to load a particular software version at step 408, it is the control console that loads the determined software version, e.g., matching the software version of the new subsystem. After loading the determined software version on the control console, the control console can validate the software configuration for the system as a whole prior to initializing the surgical system for use, e.g., to perform one or more surgical procedures.

If a second control console is available and not in need of loading new software in response to the new subsystem, the second control console may retain control of the existing subsystems and control the new subsystem while the other control console is being configured.

For example, a surgical operation may have two surgeons, a first surgeon and a second surgeon. The first surgeon may be using a first control console to control a first patient side cart and the second surgeon may be using a second control console to control a second patient side cart. In the course of the surgery, it may be determined that a third subsystem needs to be added. When the third subsystem is added, the first control console is able to use it as-configured, but the second control console needs to be upgraded.

In this case, the second control console can load the new software version to control the third subsystem. While the second control console is in an error mode for this update, the first control console can remain in control of the first subsystem and control the third subsystem and, optionally the second subsystem.

Figure 5:
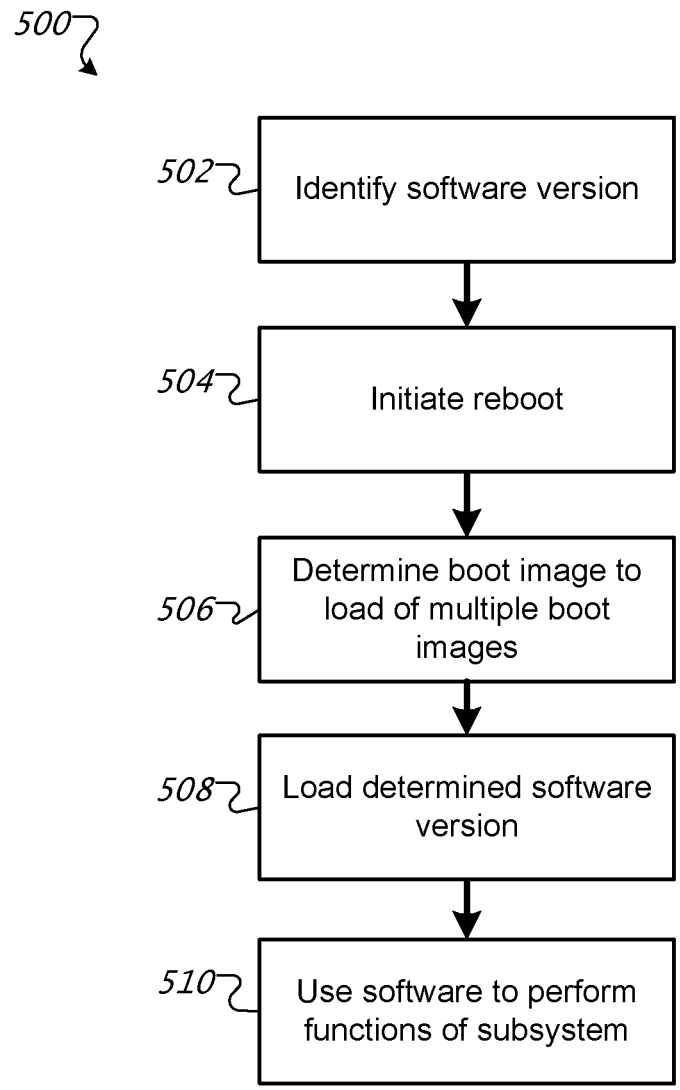
FIG. 5 is a flow diagram of an example process for loading a software version.

FIG. 5 is a flow diagram of an example process 500 for loading a software version. The process can be performed, for example, by a control console after a determination is made as to the software version to execute for a surgical system. The process can also be performed by a subsystem in response to an instruction received from the control console identifying a particular software version to execute for the surgical system.

A particular software version to be used by the subsystem, and that is not the current software version, is identified (step 502). Once the particular software version is identified, a reboot is initiated to execute the software version (step 504). In response to initiating the reboot, a determination is made as to a particular boot image or boot routine including the software version from among multiple boot images or boot routines (step 506). For example, the subsystem can include multiple boot images each having a particular software version loaded on the image. The subsystem can also include data, e.g., a file, that maps the particular boot images to the loaded software version. The subsystem can use the mapping data to determine which boot image from the multiple boot images to load. In another example, a boot routine can common to all versions can load version-specific modules. The determined software version is loaded by the subsystem (step 508). Loading images is described in greater detail with respect to FIG. 6.

After rebooting, the subsystem uses the software version loaded from the boot image to perform functions of the subsystem (step 510). For example, if the subsystem is a patient cart having one or more manipulators, the software is used to control the movements of the manipulator in response to control inputs from the control console.

Figure 6A:
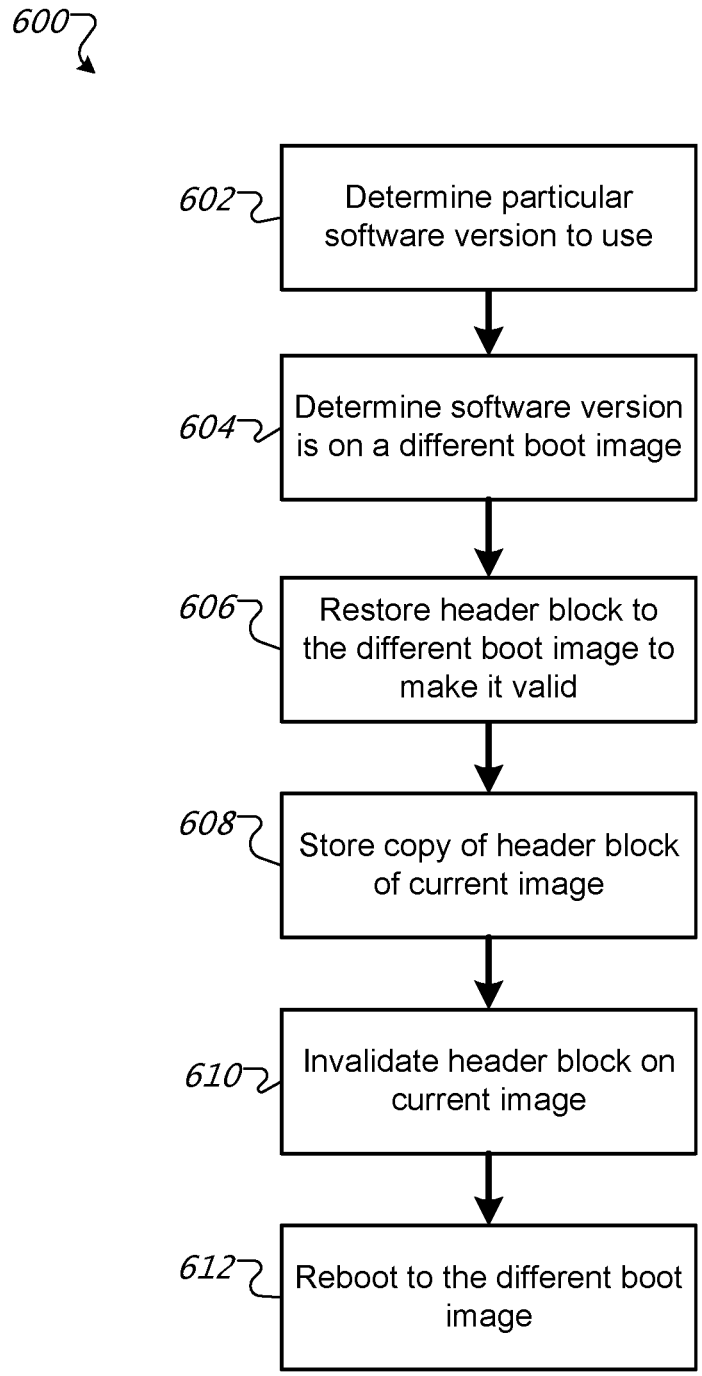
FIGS. 6A-6C are flow diagrams of an example processes for re-configuring a subsystem to a particular software version.
Figure 6B:
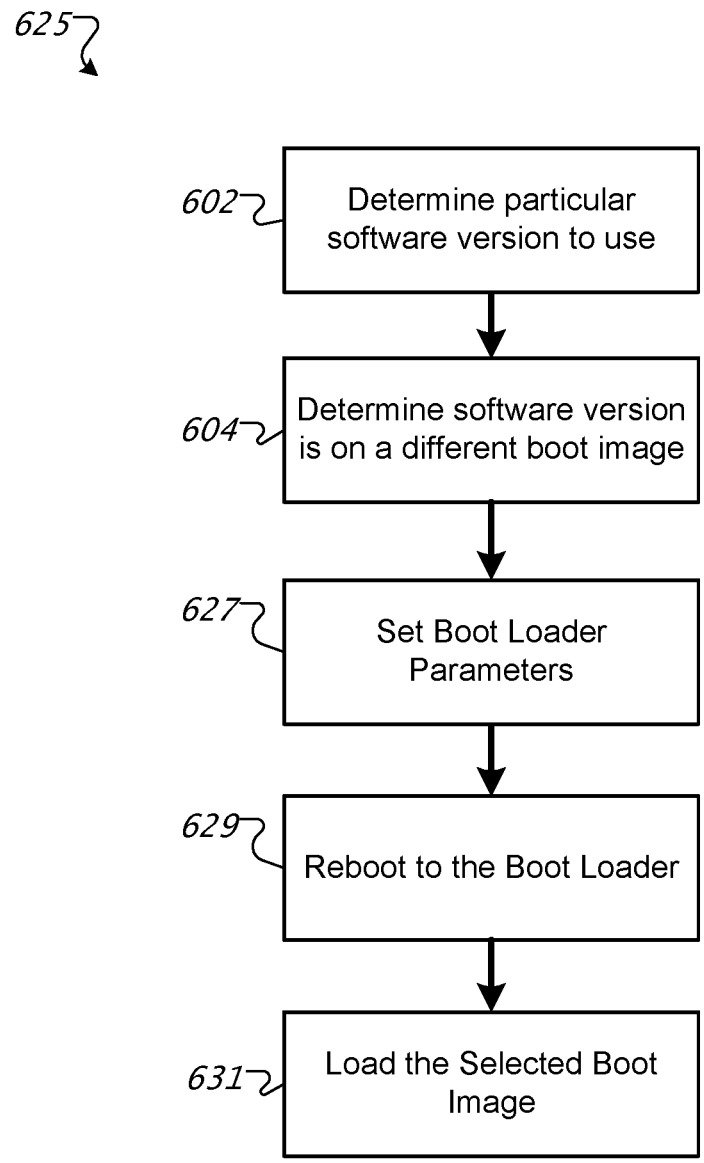
Figure 6C:
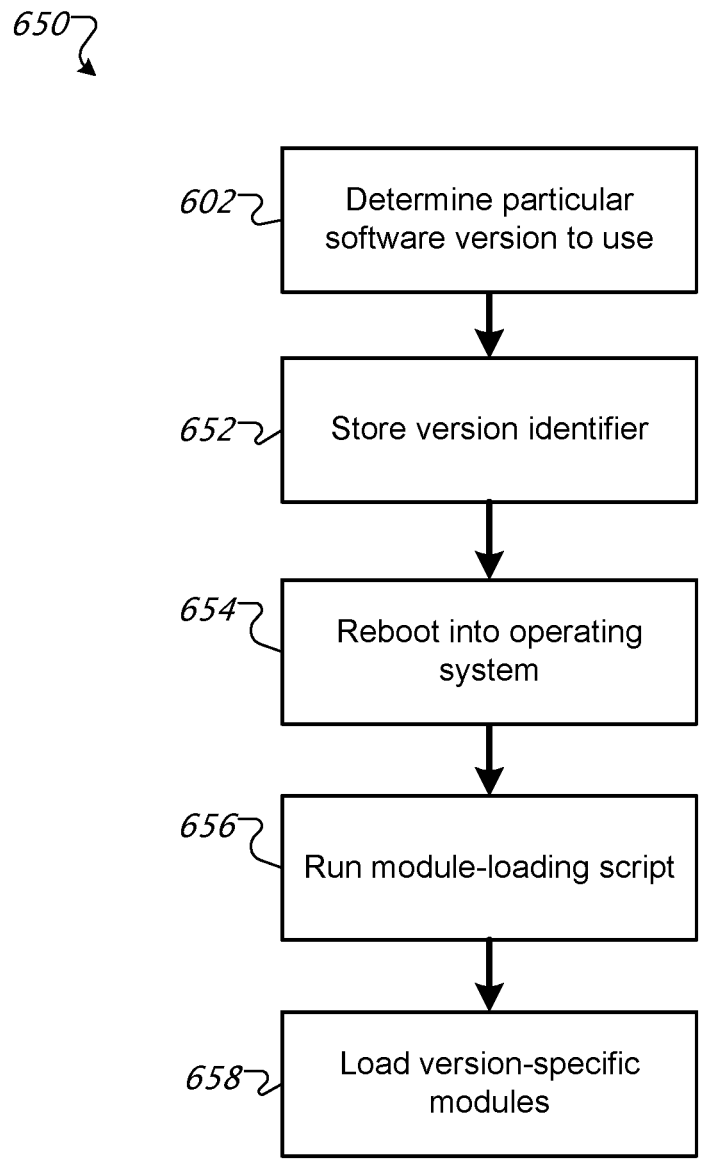

FIGS. 6A-6C are flow diagrams of example processes 600, 625, and 650 for re-configuring a subsystem to a particular software version. These processes 600, 625, and 650 can be performed, for example, by a control console or by a subsystem in response to an instruction received from the control console. The processes 600, 625, and 650 all generally can be used after the control console or subsystem after a reboot in order to load a particular software version needed for a subsystem's operation. Two different types of configurations are described. The first type of configuration, used by the processes 600 and 625, provide different boot images to access software of different version. The second type of configuration, used by the process 650, provides different modules to access software of different versions.

In the processes 600, a determination is made to use a particular software version (step 602). For example, the determination can be made by a control console determining the particular software version to be used for a surgical system or in response to a received instruction at a subsystem, e.g., by the control console, to use the particular software version. For example, a subsystem can be currently executing software version A found in boot image A. The determination can be to use software version B, which is found in boot image B.

In the process 600, a determination is made as to the location of the particular software version. In particular, if the software version is not currently being used, a determination is made that the software version is located on a different boot image than the current boot image (step 604). The control console or other subsystem can include multiple boot images. Each boot image can be associated with a particular software version that is loaded onto the boot image.

In response to determining the different boot image that contains the particular software version, a header block of the boot image is restored (step 606). In particular, each other unused boot images can have a copy of the header block stored in a storage location on the subsystem. The respective header blocks can be retrieved as needed. Thus, returning to the example, the header block of boot image B is restored from a copy of the header block from boot image B retrieved from a separate storage location. By restoring the header block, the boot image becomes bootable, e.g., by a boot loader program on the subsystem.

A copy of a header block of the current boot image is stored (step 608). For example, the copy of the header can be stored with the copied header blocks of the other unused boot images. In particular, following the example, the header block of boot image A is copied to a storage location.

The header block of the current boot image is invalidated (step 610), for example, by zeroing the header block. After the header block of boot image A is invalidated, boot image A can no longer be booted in response to a restart. However, now that the header has been restored to boot image B, a restart will boot from boot image B, which in turn will load software version B. The subsystem is rebooted to the different boot image (step 612).

In some scenarios, an interrupt occurs during the reconfiguration process described with respect to the process 600. In those scenarios, the system determines which boot image to load depending on the status of the process. Because of the sequence of restoring the header block to the different boot image before zeroing out the current boot image, there will always be at least one valid boot image available to load at restart in case of an interrupt.

For example, if the interrupt occurs before the header has been restored to boot image B, the header for boot image A is still valid while the boot image B is not valid. Upon restarting after the interrupt, the subsystem determines to boot to boot image A and the switch to boot image B can be reattempted, e.g., the header to boot image B can be restored and the header for boot image A can be invalidated as described above.

In another example, if the interrupt occurs after the header has been restored to the boot image B and after the header block of boot image A has been zeroed, then only boot image B is valid. Upon restarting the subsystem determines to boot to boot image B and load the corresponding software version.

In another example, if the interrupt occurs after the header has been restored to the boot image B and before the header block of boot image A has been zeroed, then both boot image A and boot image B are valid. The subsystem determines which boot image to load from the two valid boot images according to one or more criteria. For example, the subsystem can default to the last loaded boot image, in this example boot image A. After loading boot image A, the subsystem can determine that the change to boot image B is still needed and proceed with the process for changing the valid boot image to boot image B. Other criteria for determining which boot image to load can be used. For example, the subsystem can use the lowest-numbered valid boot image or choose among valid boot images randomly.

In the process 625, after a determination is made to use a particular software version (step 602), a determination is made that the software version is located on a different boot image than the current boot image (step 604). Unlike in the process 600 in which a boot image headers are used to control the boot image used after a reboot, the process 625 uses a boot loader that is able to select from multiple available boot images in order to load the selected software version.

The boot loader is given parameters that identify the boot image that corresponds to the particular software version needed (step 627). For example, the control console can store these parameters in non-volatile computer memory accessible by the boot loader, or can send the parameters to the subsystem for storage in such a memory.

With the parameters identifying the selected boot image stored, a restart will boot into the boot loader (step 629). The boot loader can proceed to execute the instructions of booting, including loading the selected boot image (step 631). For example, the boot loader may read the contents of the computer memory to retrieve the parameters that identify which boot image to boot into, and then boot into that boot image.

In the process 650, after a determination is made to use a particular software version (step 602), a determination is made that different version-specific modules are needed. Unlike in the processes 600 and 625 in which different boot images are used to gain access to different software, the process 650 boots into the same operating system regardless of software version needed. Then, version-specific modules are loaded.

A version identifier is stored (step 652). For example, the control console can store the desired version in a computer memory that will be accessible by the operating system after reboot, or can send the version to the subsystem for storage in such a memory.

With the version indicator stored, a restart will boot into the operating system (step 654). This reboot has the effect of loading the operating system without any version-specific module loaded. The operating system may provide some functionality such as retrieval of data from memory, network communications, or diagnostic functions. However, without any version-specific modules loaded, limited control, or no control, of a corresponding sub-system. In some cases, other ways of reconfiguring the operating system may be used. For example, instead of rebooting, the some or all of the software modules may be unloaded. This may allow, for example, continuous operation of operating system or unrelated application in the operating system, which may be interrupted by a reboot.

The operating system may run a module-loading script (step 656). For example, the operating system may be configured to run one or more scripts stored in a particular directory as part of starting up, or in response to completing the startup process. This script may include instructions to read the version indicator from computer memory and load the version-specific module (step 658). These version-specific modules then provide the same or similar functionality to the control console and subsystems that the boot images in the processes 600 and 625. The version-specific modules can include applications, libraries, services, or other software objects that are compatible with the operating system.

In some implementations, one or more boot images or modules can be downloaded from a network location as needed. For example, in response to determining that a particular software version is to be used, but that is not currently stored on the subsystem, a corresponding boot image can be downloaded into memory on the subsystem. The downloaded boot image can then be switched to the current boot image as described above.

In some implementations, the surgical system can connect to additional accessories as long as the hardware configuration is valid for use with the surgical system. For example, a second control console can be connected to the system. The second control console can be used as a training device during a procedure or for independently operating one or more surgical instruments, e.g., during a complex procedure. A first control console having overall control for the system setup can determine the software version for the second control console and provide corresponding instructions to the second control console to load the software version. Other accessories can be used, for example, an additional manipulator that is not specific to a particular surgical system.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include master and one or more slave devices. The master and slave devices are generally remote from each other and typically interact through a communication network. The relationship of master and slave arises by virtue of computer programs running on the respective computers and having a master-slave relationship to each other. In some embodiments, a master transmits data e.g., control commands to a slave device (e.g., for purposes of moving a surgical instrument). Data generated at the slave device (e.g., camera images) can be returned to the master device.

In some embodiments, the joints of the manipulator can include active and passive joints. An active joint is a joint whose motion is controlled by power provided from within the surgical system, for example, by a motor associated with the joint. A passive joint is one that move solely from power provided outside the system, or more simply, a non-powered joint. An active joint does not need to be teleoperated or robotically controlled. Movement of the active joints can be provided by one or more associated motors. In some implementations, the motors are brushless direct current electric motors. In some other implementations, servo-mechanisms are used to control active joints in a closed loop feedback system. When a surgeon provides input to a master controller for a particular manipulator, the movements are calculated such that the surgeon can operate the surgical instrument at a specific location.

For safety reasons, the joints of the manipulator for use in a surgical system generally include locking mechanisms to prevent uncontrolled movement of the manipulator. In some implementations, the locking is provided by brakes that are engaged when power is removed from the brakes. Examples of these types of brakes include electromechanical or electromagnetic locks. In some implementations, these brakes can be released to allow manual, unpowered, movement of the manipulator.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method comprising:
    obtaining, at a control subsystem associated with a surgical system, a hardware configuration from a first patient side subsystem of the surgical system, wherein the first patient side subsystem is communicatively coupled to and controlled by the control subsystem;
    determining, with a data processing apparatus, a software version to be used by the control subsystem and the first patient side subsystem, wherein determining the software version includes selecting the software version from among a plurality of software versions, and wherein each software version of the plurality of software versions is associated with a particular patient side subsystem;
    instructing, with the data processing apparatus, the first patient side subsystem to use the software version;
    determining, with the data processing apparatus, whether the software version is currently loaded on the control subsystem;
    in response to determining that the software version is not currently loaded on the control subsystem, loading, with the data processing apparatus, the software version on the control subsystem;
    validating, with the data processing apparatus, the software version loaded on the control subsystem and the first patient side subsystem;
    initializing, with the data processing apparatus, the surgical system with the software version;
    receiving, at the first patient side subsystem, an instruction to load the software version;
    determining that the software version is located on a second configuration different from a first configuration currently loaded on the first patient side subsystem;
    storing data corresponding to the second configuration; and
    configuring the first patient side subsystem to the second configuration.

2. The method of claim 1, further comprising validating, with the data processing apparatus, the hardware configuration of the first patient side subsystem prior to determining the software version to be used by the control subsystem and the first patient side subsystem.

3. The method of claim 2, wherein validating the hardware configuration includes: determining that the hardware configuration is compatible with the control subsystem.

4. The method of claim 1, wherein the control subsystem comprises components of a surgeon console of the surgical system, wherein the surgeon console is configured to provide control functions to an operator of the surgical system, and wherein the first patient side subsystem includes one or more manipulators configured to hold and position one or more corresponding surgical instruments.

5. The method of claim 1, wherein instructing the first patient side subsystem to use the software version comprises: loading the software version on the first patient side subsystem by:
    determining one or more particular modules of multiple modules, wherein the particular modules contain the software version; and
    loading the particular modules.

6. The method of claim 1, wherein the determining the software version to be used by the control subsystem and the first patient side subsystem is performed based on a collaboration between the control subsystem and the first patient side subsystem.

7. The method of claim 1, wherein validating the software version comprises:
    determining whether the control subsystem and the first patient side subsystem have loaded the software version; and
    in response to determining that the control subsystem or the first patient side subsystem has not loaded the determined software version, generating an error message and preventing initialization of at least one of: the control subsystem and the first patient side subsystem for use in the surgical system.

8. The method of claim 1, further comprising:
recognizing, with the data processing apparatus, that a second patient side subsystem has been communicatively coupled to the controller subsystem;
obtaining, with the data processing apparatus, hardware information about the second patient side subsystem;
validating, with the data processing apparatus, the hardware information of the second patient side subsystem; and
instructing, with the data processing apparatus, the second patient side subsystem to load the software version.

9. The method of claim 1, further comprising:
recognizing, with the data processing apparatus, that a second patient side subsystem has been communicatively coupled to the control subsystem;
obtaining, with the data processing apparatus, hardware information about the second patient side subsystem;
validating, with the data processing apparatus, the hardware information of the second patient side subsystem; and
loading, with the data processing apparatus, a second software version on the control subsystem, wherein the second software version corresponds to software loaded on the second patient side subsystem.

10. The method of claim 1, wherein the software version is determined based on a current software version currently loaded on the controller subsystem or on the first patient side subsystem.

11. The method of claim 1, further comprising downloading the second configuration.

12. The method of claim 1, further comprising, in response to an interrupt:
determining a valid software version from the software version and a previously loaded software version; and
rebooting the control subsystem or the first patient side subsystem to the valid software version.

13. A method comprising:
obtaining, at a control subsystem associated with a surgical system, a hardware configuration from a first patient side subsystem of the surgical system, wherein the first patient side subsystem is communicatively coupled to and controlled by the control subsystem;
determining, with a data processing apparatus, a software version to be used by the control subsystem and the first patient side subsystem, wherein determining the software version includes selecting the software version from among a plurality of software versions, and wherein each software version of the plurality of software versions is associated with a particular patient side subsystem;
instructing, with the data processing apparatus, the first patient side subsystem to use the software version;
determining, with the data processing apparatus, whether the software version is currently loaded on the control subsystem;
in response to determining that the software version is not currently loaded on the control subsystem, loading, with the data processing apparatus, the software version on the control subsystem;
validating, with the data processing apparatus, the software version loaded on the control subsystem and the first patient side subsystem;
initializing, with the data processing apparatus, the surgical system with the software version
wherein instructing the first patient side subsystem to use the software version comprises: loading the software version on the first patient side subsystem by:
determining a particular boot image of multiple boot images, wherein the particular boot image contains the software version; and
rebooting the first patient side subsystem from a current boot image to the particular boot image,
wherein rebooting the first patient side subsystem from the current boot image to the particular boot image comprises:
obtaining a first header block for the particular boot image;
restoring the obtained first header block to the particular boot image;
storing a copy of a second header block for the current boot image; and
after restoring of the obtained first header block and storing of the copy of the second header block, invalidating the second header block for the current boot image.

14. A system, comprising:
a control subsystem, wherein the control subsystem is configured to communicatively couple with a plurality of patient-side subsystems, wherein each patient-side subsystem is associated with a software configuration of a plurality of software configurations, and
wherein the control subsystem configures the system by:
determining a combination of the control subsystem communicatively coupled with a particular patient-side subsystem of the plurality of patient-side subsystems,
selecting a particular software configuration from the plurality of software configurations based on the combination,
initializing the system after validating the particular software configuration;
transmitting instructions from the control subsystem to the particular patient-side subsystem to load the particular software configuration, wherein the particular patient-side subsystem is configured to:
receive the instruction to load the software version;
determine that the software version is located on a second configuration different from a first configuration currently loaded on the particular patient side subsystem
store data corresponding to the second configuration; and
configure the particular patient side subsystem to the second configuration.

15. The system of claim 14, wherein the particular patient-side subsystem has a particular hardware configuration and wherein the control subsystem determines the particular hardware configuration is valid for the combination of the control subsystem communicatively coupled with the particular patient-side subsystem prior to determining the particular software configuration.

16. The system of claim 14, wherein the control subsystem comprises components of a surgeon console of a surgical system, wherein the surgeon console is configured to provide control functions to an operator of the surgical system, and wherein the particular patient-side subsystem includes one or more manipulators configured to position one or more corresponding surgical instruments responsive to user input to the control subsystem.

* * * * *